United States Patent [19]

Prahl

[11] 4,409,972
[45] Oct. 18, 1983

[54] MOULDING PART FOR MAKING RELIEVING AND SUPPORTING PLASTER BANDAGES, MORE PARTICULARLY IN THE UPPER ZONE OF THE HUMAN THIGH, AND PLASTER BANDAGE MADE USING SUCH MOULDING PART

[75] Inventor: Jan Prahl, Rullstorf, Fed. Rep. of Germany

[73] Assignee: Firma IPOS Gesellschaft für Integrierte Prothesen-Entwicklung und Orthopädietechnischen Service mbH & Co. KG, Luneburg, Fed. Rep. of Germany

[21] Appl. No.: 296,077

[22] Filed: Aug. 25, 1981

[30] Foreign Application Priority Data

Aug. 27, 1980 [DE] Fed. Rep. of Germany ....... 3032194

[51] Int. Cl.³ ............................................ A61F 13/04
[52] U.S. Cl. ....................................... 128/91 R; 3/19
[58] Field of Search .............. 128/80 R, 83, 85, 87 R, 128/89 R, 89 A, 90, 91 R, 157, 165, 518 R, 521, 523-525, 577; 3/2, 17 R, 17 SS, 18-21

[56] References Cited

U.S. PATENT DOCUMENTS

| 2,002,064 | 5/1935 | Kohl | 3/19 |
| 2,253,040 | 8/1941 | Martino | 3/17 R X |
| 2,594,751 | 4/1952 | Fahlstrom | 3/17 R |
| 3,040,740 | 6/1962 | Parker | 128/83 |
| 3,823,208 | 7/1974 | Asbelle et al. | 3/17 R X |
| 4,274,166 | 6/1981 | Chambers | 128/90 X |

Primary Examiner—Lee S. Cohen
Assistant Examiner—Angela D. Sykes
Attorney, Agent, or Firm—Toren, McGeady and Stanger

[57] ABSTRACT

A moulding part for making relieving and supporting plaster bandages, which is constructed like a clasp in the form of an unclosed ring, one of whose circularly extending edges extends at an inclination and has a laterally projecting edge bead and which has a bending-resilient supporting clasp worked into the material of the moulding member in the mould supporting zone, for the production of relieving and supporting plaster bandages in which impact loadings acting on the plaster bandage are absorbed by means of the moulding member.

4 Claims, 4 Drawing Figures

MOULDING PART FOR MAKING RELIEVING AND SUPPORTING PLASTER BANDAGES, MORE PARTICULARLY IN THE UPPER ZONE OF THE HUMAN THIGH, AND PLASTER BANDAGE MADE USING SUCH MOULDING PART

The invention relates to a moulding part for making relieving and supporting plaster bandages, more particularly in the zone of the upper part of the human thigh, and to a plaster bandage made using this protective member, that is, the moulding part.

When making relieving and supporting plaster bandages for the legs, Clinics require particularly suitable moulds for the zone of the upper part of the thigh. These functional forms must take the weight of the patient's body and distribute the load uniformly in the moulding part.

It has been found that a primary Tuber support is necessary, and so is a support in the front zone of the Quadriceps. Both supporting surfaces must extend at an inclination to one another in the direction of the medial side and leave the strongly marked parts of the Vastus laterales and the Luteus maximus free on the lateral side. However, one disadvantage is that the making of such relieving and supporting plaster bandages requires trained specialists to be available who are able to call on rich experience to make a relieving ring which is satisfactory from the aspect of plastering technique.

It is therefore an object of the invention to provide for relieving and supporting plaster bandages a thigh moulding ring which affords resilient support in the groin and seat ring zone, absorbs impact loadings exerted on the plaster bandage, and enables relieving rings to be readily produced in relieving and supporting plaster bandages of the kind specified.

To solve this problem the invention provides a moulding part for making relieving and supporting plaster bandages, more particularly in the zone of the upper part of the human thigh, wherein the moulding part has a moulding member, constructed like a clasp in the form of an unclosed ring, one of whose two end-side edge zones extends at an inclination to the other edge zone and has a laterally projecting edge bead which merges into the moulding member wall in the higher zone of the moulding member, which has in the mould supporting zone a supporting clasp of a bending-resilient metal material worked into the material of the moulding member.

The invention also provides a relieving and supporting plaster bandage, more particularly in the zone of the upper part of the human thigh, using a knitted tube applied to the inner wall surface of the plaster sleeve, wherein the plaster sleeve of the plaster bandage has at its end adjacent the groin and seat ring zone between the knitted tube and the plaster sleeve a moulding member which is integrated in the plaster bandage and which is constructed like a clasp and an unclosed ring and one of whose two end-side edge zones extends at an angle to the other edge zone and has a laterally projecting edge bead which merges into the moulding member wall in the higher zone of the moulding member, which has in the mould supporting zone a supporting clasp of bending-resilient metal material worked into the material of the moulding member, the knitted tube extending out of the interior being pulled over the edge bead of the moulding member and plastered into the last plaster layer.

The invention also provides the use of a moulding ring, comprising a clasp-like, ring-like moulding member having an end-side moulded-on edge bead and a ring-like supporting clasp of bending-resilient metal material which is worked into the material of the moulding member in the mould supporting zone, for making relieving and supporting plaster bandages, more particularly in the zone of the upper part of the human thigh, in order to obtain a resilient support in the groin and seat ring zone, while at the same time absorbing impact loadings on the plaster bandage.

A moulding part thus constructed enables a relieving and supporting plaster bandage to be readily made with a relieving ring in the zone of the upper part of the human thigh without the need for skilled specialists. In accordance with practice, a relieving and supporting plaster bandage of the kind specified is applied by a knitted cotton tube being pulled over the leg. The moulding ring is then slipped over the tube and moved into the correct supporting position. It is important to take into account accurately the different individual peripheries of the thigh in the supporting zone. For this reason the moulding part is constructed functionally like a clasp and has a firmly cast-in metal support which can be individually bent wider or narrower without the basic supporting shape being changed. When a thigh moulding ring of the kind specified has been adapted to its intended final width and moved into the correct position, the plaster bandage is applied in known manner over the moulding ring. The moulding part is anchored in the plaster material via the edge bead. The result is in the groin and seat ring zone a resilient support which is outstandingly suitable for absorbing impact stressing of the modelled plaster, thus ensuring comfortable wearing on the body. At the same time the difficult work of moulding supporting plaster is practically eliminated. With the thigh moulding ring functionally correct leg plasters can be produced by simple circular plastering-in. After the last layers of plaster, the knitted tubular skin, which extends out of the interior of the supporting plaster, is pulled around the plaster and plastered in with the last layer.

DESCRIPTION OF THE DRAWINGS

The invention is illustrated by way of examples in the drawings, wherein.

DETAILED DESCRIPTION OF THE PREFERRED EMBODIMENTS

Figure 1:
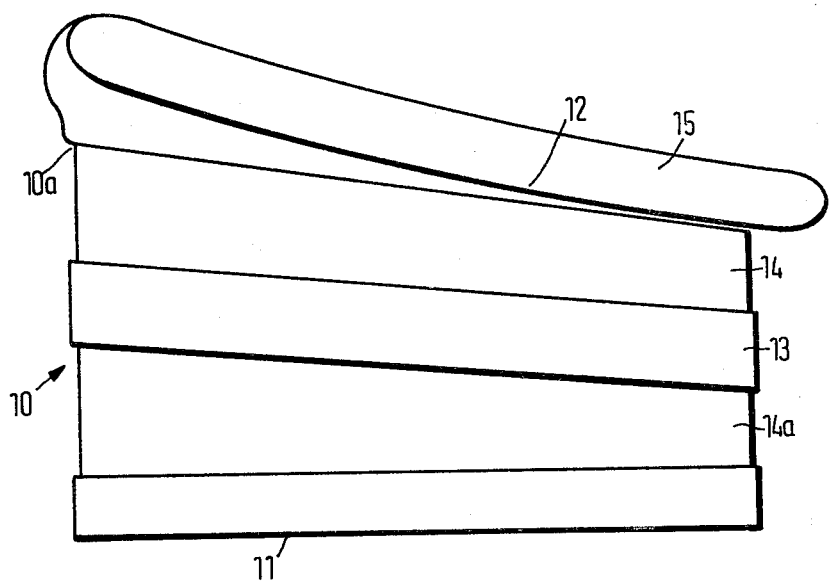
FIG. 1 is a lateral elevation of a moulding part for making relieving and supporting plaster bandages.
Figure 2:
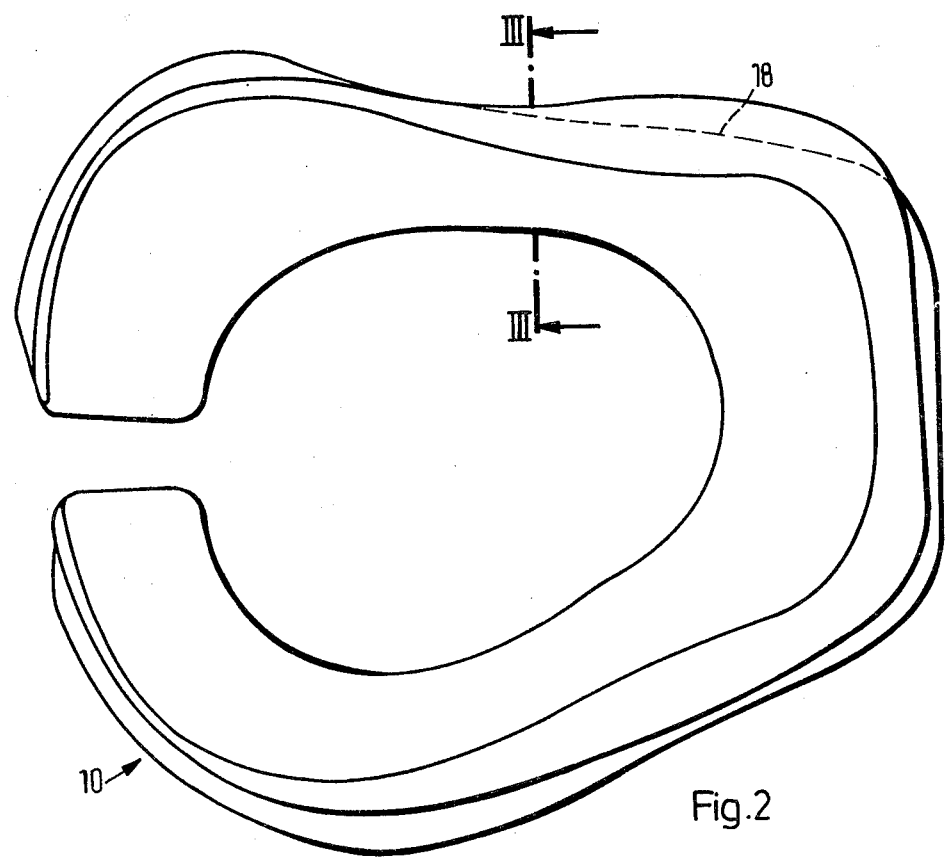
FIG. 2 is a plan view of the moulding part.
Figure 3:
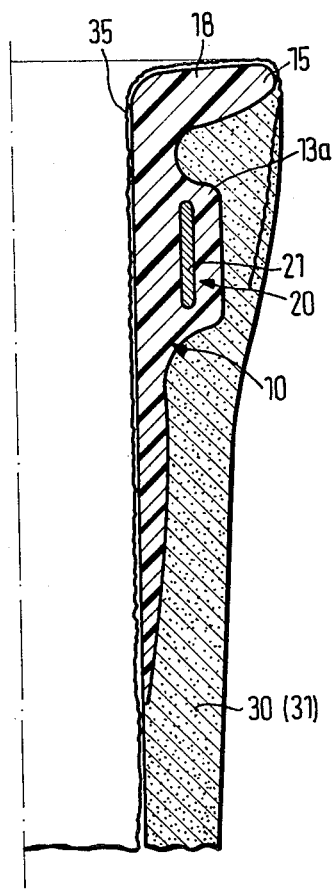
FIG. 3 is a vertical section, taken along the line III—III in FIG. 2.

In the embodiment illustrated in FIGS. 1–3 a moulding part used for making and relieving and supporting plaster bandages comprises a moulding member 10, which is constructed like a clasp in the form of an unclosed ring and is preferably made of an addition cross-linked toxicologically harmless silicon rubber. The moulding member 10 is therefore constructed like a sleeve, but cut open, so that the clasp-like function is maintained.

The two end-side edge zones of the moulding member 10, have the references 11 and 12 and its outer wall surface has the reference 13. The upper edge zone 12 of the moulding member 10 is so constructed that the plane formed by the edge zone 12 extends at an inclination to the lower edge zone 11. Formed on the upper edge zone 12 is an outwardly projecting edge bead 15 which merges into the wall surface 13 of the moulding member 10 in the higher zone 10a. The outer wall surface 13 of the moulding member 10 is also formed with one or more annular grooves 14, 14a, via which the moulding member 10 is anchored in the plaster of a plaster bandage 30.

Adjacent to the upper edge zone 12—i.e. below the edge bead 15—a supporting clasp 21 of bending-resilient metal or similar suitable material, which is disposed in an outwardly projecting zone of reinforced material 13a and can also be made, more particularly, of aluminium (FIG. 3) is disposed in the material of the moulding member 10. The supporting clasp 21 is anchored in the moulding member 10 and enables the moulding part to be shaped and adapted to the thigh without the basic supporting shape being altered. This enables the thigh shaping ring to be adapted to the necessary width in each case.

Figure 4:
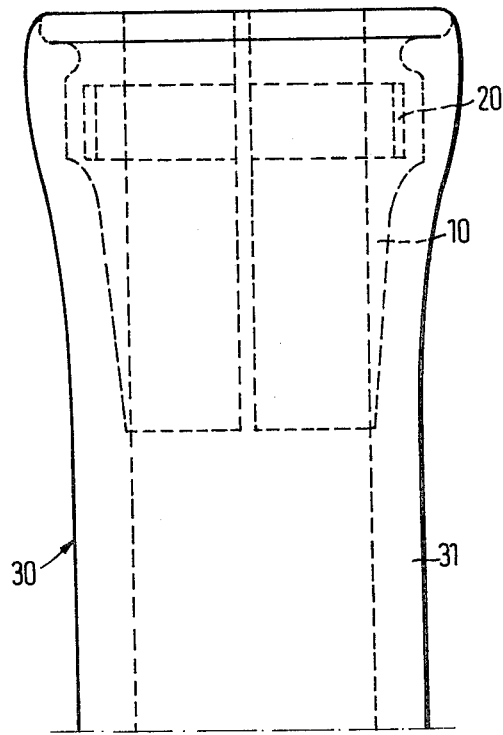
FIG. 4 is a plan view of the plaster sleeve of a relieving and supporting plaster bandage with a moulding part disposed at the end side.

As shown in FIG. 4, the moulding member 10 has a metal anchoring 20. A tuber bench is formed on the moulding member 10.

FIG. 4 shows a relieving and supporting plaster bandage 30 with a moulding part constructed according to the invention. The moulding member 10 of the moulding part is plastered into the plaster sleeve 31 of the plaster bandage 30. The more particularly cotton knitted tube 35 extends outwards on the end side and is laid around the moulding member 10. The free end of the knitted tube 35 is plastered into the top layer of the plaster bandage 30.

What is claimed is:

1. A moulding part for making relieving and supporting plaster bandages, for use in the zone of the upper part of the human thigh, wherein the moulding part has a moulding member having an inner surface and an outer surface, said moulding member being and constructed like a clasp in the form of an unclosed ring arranged to extend around the thigh, said moulding member having an upper end-side edge zone extending transversely of the ring axis of said moulding member and a lower end-side edge zone, said upper end-side edge zone being inclined relative to said lower end-side edge zone and having a laterally outwardly projecting edge bead which projects outwardly from and merges into the outer surface of said moulding member adjacent said upper end-side edge zone of the moulding member, an outwardly projecting mould supporting zone formed with and encircling said moulding member at a space below said edge bead, a supporting clasp located in the mould supporting zone and formed of a bending-resilient metal material positioned within the material of the moulding member.

2. A moulding part according to claim 1, wherein at least one annular groove is formed in the outer surface of the moulding member located between said edge bead and said outwardly projecting mould supporting zone.

3. A moulding part according to claim 1, wherein the moulding member is made of an addition cross-linked, toxicologically harmless silicon rubber.

4. A relieving and supporting plaster bandage, for use in the zone of the upper part of the human thigh, comprising a plaster sleeve having an upper end and a lower end relative to the thigh and an inside surface and an outside surface, a knitted tube which is laid against the inside surface of the plaster sleeve, a moulding member integrated in the plaster sleeve of the plaster bandage at its upper end between the knitted tube and the plaster sleeve, said moulding member being constructed like a clasp in the form of an unclosed ring arranged to extend around the thigh, said moulding member having an upper end-side edge zone extending transversely of the ring axis of said moulding member and a lower end-side edge zone, said upper end-side edge zone is inclined relative to said lower end-side edge zone and has a laterally outwardly projecting edge bead which projects outwardly from and merges into the outer surface of said moulding member adjacent said upper end-side edge zone of the moulding member, an outwardly projecting mould supporting zone formed with and encircling said moulding member at a space below said edge bead, a supporting clasp located in the mould supporting zone and formed of a bending-resilient metal material positioned within the material of the moulding member.

* * * * *